United States Patent
Yamaguchi et al.

(10) Patent No.: US 7,196,203 B2
(45) Date of Patent: Mar. 27, 2007

(54) PHENOL DERIVATIVES AND METHOD OF USE THEREOF

(75) Inventors: Toshiaki Yamaguchi, Matsumoto (JP); Masaaki Ban, Hotaka-machi (JP); Takashi Yanagi, Hotaka-machi (JP); Ken Kikuchi, Fukui (JP); Minoru Kubota, Fukui (JP); Tetsuji Ozawa, Hotaka-machi (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/520,426

(22) PCT Filed: Jun. 26, 2003

(86) PCT No.: PCT/JP03/08085

§ 371 (c)(1),
(2), (4) Date: Jan. 7, 2005

(87) PCT Pub. No.: WO2004/005251

PCT Pub. Date: Jan. 15, 2004

(65) Prior Publication Data

US 2005/0209486 A1    Sep. 22, 2005

(30) Foreign Application Priority Data

Jul. 8, 2002    (JP)    ............................... 2002-199311

(51) Int. Cl.
*C07D 209/48*    (2006.01)
(52) U.S. Cl. ...................................... 548/473; 564/338
(58) Field of Classification Search ................ 564/338; 548/473
See application file for complete search history.

(56) References Cited

U.S. PATENT DOCUMENTS 3,278,600 A    10/1966    L'Italien
4,226,803 A    10/1980    Klingler et al.

FOREIGN PATENT DOCUMENTS

GB    2 011 389 A    7/1979
JP    50-137911 A2    11/1975

OTHER PUBLICATIONS

CA abstract of Mueller et al., Archiv der Pharmazie und Berichte der Deutschen Pharmazeutischen Gesellschaft (1968), 301(2), 161-7, STN search result.*
Chiral HPLC Column Products introduction from Chromtech company.*
Chemical Abstracts; vol. 69, abs. No. 43560.
Chemical Abstracts, vol. 63, abs No. 8235a-f.
Caroll Temple, et al.; Antimitotic Agents. Chiral Isomers of Ethyl[5-Amino-1,2-dihydro-3-(4-hydroxyphenyl)-2-methylpyrido [3,4-*b*]pyrazin-7-yl]carbamate; J. Med. Chem.1992, 35, 989-993.

* cited by examiner

*Primary Examiner*—Kamal A. Saeed
*Assistant Examiner*—Yong Chu
(74) *Attorney, Agent, or Firm*—Sughrue Mion, PLLC

(57)    ABSTRACT

The present invention provides novel phenol derivatives represented by the formula:

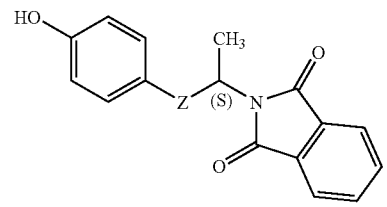

wherein the carbon atom marked with (S) represents a carbon atom in S configuration; Z represents the group represented by the formula:

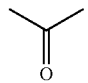

or the formula:

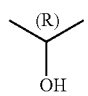

wherein the carbon atoms marked with (R) represents a carbon atom in R configuration, and a method to produce a phenol derivative represented by the formula (A):

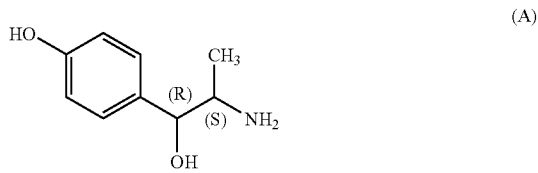

(wherein the carbon atom marked with (R) and (S) have the same meanings as defined above) which comprises using any of those derivatives as an intermediate therefore.

5 Claims, No Drawings

PHENOL DERIVATIVES AND METHOD OF USE THEREOF

TECHNICAL FIELD

The present invention relates to phenol derivatives and method of use thereof.

More particularly, the present invention relates to novel phenol derivatives represented by the general formula:

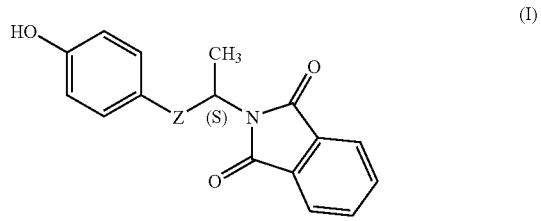

(I)

wherein the carbon atom marked with (S) represents a carbon atom in S configuration; Z represents the group represented by the formula:

or the formula:

wherein the carbon atom marked with (R) represents a carbon atom in R configuration, and method of use thereof.

BACKGROUND ART

The optically active phenol derivative, more particularly, the phenol derivative (chemical name: (1R, 2S)-2-amino-1-(4-hydroxyphenyl)propan-1-ol) represented by the formula:

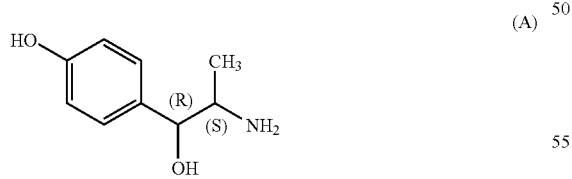

(A)

(wherein the carbon atoms marked with (R) and (S) have the same meanings as defined above) which is watched as an intermediate of medicaments and described to be useful in manufacturing, for example, 2-aminopropanol derivatives useful as agents for prevention or treatment of obesity, hyperglycemia or a disease caused by intestinal tract hypermotility (see the following literature 1), aminoethylphenoxyacetic acid derivatives useful as agents for pain remission and calculi removal promotion in urinary lithiasis (see the following literature 2), and phenoxyacetic acid derivatives useful as agents for prevention or treatment of pollakiuria, urinary incontinence, depression, biliary calculi or a diseases caused by hypermotility of biliary tract (see the following literature 3).

Thus far, as a production method of the optically active compound represented by the above formula (A), a method to obtain the compound represented by the above formula (A) by optical resolution with (−)-D-tartaric acid from a mixture of enantiomeric isomers represented by a formula:

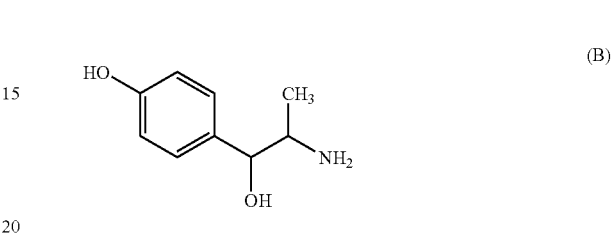

(B)

(wherein the relative configuration of the amino group and the hydroxy group is erythro configuration) has been reported (see the following literature 4).

However, in the above method to produce the phenol derivative represented by the above formula (A), the mixture of the enanthiomeric isomers represented by the above formula (B) has to be optically resolved by using unnatural (−)-D-tataric acid unavailable easily, and in addition, the yield of the obtained phenol derivative represented by the above formula (A) is rather low of about 19%. Furthermore, it was an extremely wasteful method in that, for example, the most of the produced phenol derivative represented by the above formula (B) was wasted, because in the optical resolution of the mixture of enantiomeric isomers represented by the above formula (B), the other isomer of a desired isomer could not be recycled.

As mentioned above, the method that has been ever reported to produce the optically active phenol derivative represented by the above formula (A) has many problems, and is not a necessarily satisfactory production method in manufacture on an industrial scale and from the viewpoint of environmental aspects. Therefore, more effective and efficient method to produce the optically active phenol derivative represented by the above formula (A) has been desired.

Literature 1: JP Publication No. 2001-114736
Literature 2: WO99/05090 pamphlet
Literature 3: WO00/02846 pamphlet
Literature 4: Smith, Howard E., and other 4, Agonist effects of β-phenethylamines on the noradrenergic cyclic adenosine 3',5'-monophosphate generating system in rat limbic forebrain., Journal of Medicinal Chemistry, 1977, Vol.20, No. 7, p. 978–981.

DISCLOSURE OF INVENTION

The present inventors have studied earnestly to find a suitable method for manufacturing the optically active phenol derivative useful as a production intermediate of medicaments, represented by the above formula (A), and as a result, found a method to produce the compound represented by the above formula (A) more easily, effectively, and efficiently than before. The present invention has been completed based on the knowledge obtained in the production process.

The present invention is to provide a novel intermediate suitable for manufacture of, for example, an optically active phenol derivative represented by the above formula (A) that is useful as a production intermediate for various medicaments and a method of use thereof.

That is, it was found that an optically active phenol derivative found newly by the present inventors, represented by the formula:

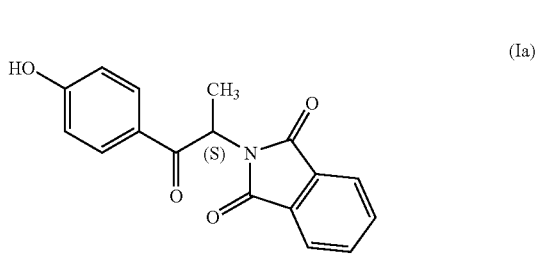

(Ia)

(wherein the carbon atom marked with (S) has the same meaning as defined above), can be stereoselectively reduced into a highly pure phenol derivative represented by the formula:

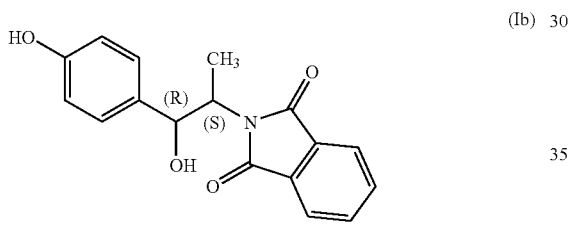

(Ib)

(wherein the carbon atoms marked with (R) and (S) have the same meanings as defined above) without using any special asymmetric catalyst unavailable easily, and furthermore, by treating the obtained phenol derivative represented by the above formula (Ib) with an amine such as methylamine or hydrazine, without conducting optical resolution, the highly pure optically active phenol derivative (A) can be produced more easily, effectively and efficiently than before.

The compounds of the present invention represented by the above formula (Ia) and (Ib) can be prepared, for example, in a manner described in Scheme 1.

Scheme 1

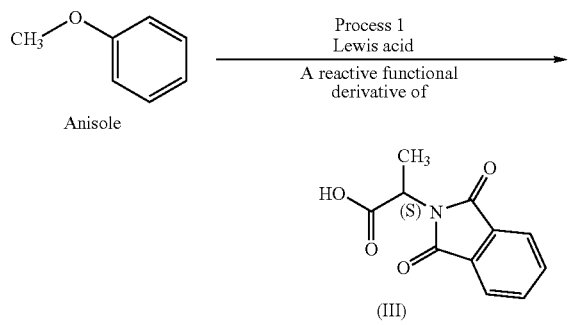

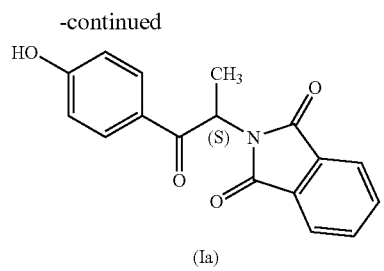

(Ia)

Process 2
Catalytic reduction

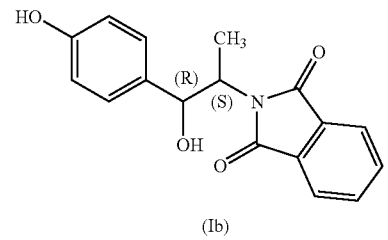

(Ib)

(wherein the carbon atoms marked with (R) and (S) have the same meanings as defined above.)

Process 1

A phenol derivative (Ia) can be obtained by subjecting a reactive functional derivative typified by an acid halide of (S)-2-phthalimidopropionic acid (III) to reaction with anisole in a presence of a Lewis acid in an organic solvent such as chlorobenzene, dichloromethane or 1,2-dichloroethane usually at 40° C. to 80° C. for 3 to 24 hours. As a reactive functional derivative, it is preferable to use 0.5 to 1.5 equivalent of (S)-2-phthalimidopropionyl chloride. As a Lewis acid, it is preferable to use 3.5 to 5.0 equivalent of aluminum chloride.

Process 2

A compound (Ib) can be obtained by subjecting the obtained compound (Ia) to catalytic hydrogenation in a presence of a palladium catalyst such as palladium-carbon powder or palladium hydroxide or a nickel catalyst such as Raney nickel in an organic solvent such as N,N-dimethylformamide, ethanol or dioxane usually at room temperature to reflux temperature of the solvent at 1 to 10 atm for 1 to 48 hours.

Optically active 2-phthalimidopropionic acid represented by the above formula (III) can be prepared from a cheap, easily available and natural (L)-alanine in a publicly known method (see the following literature 5).

From novel compounds (Ia) and (Ib) of the present invention, the optically active phenol derivative represented by the above formula (A) useful as a production intermediate of medicaments can be prepared in the following method described in Scheme 2:

Scheme 2

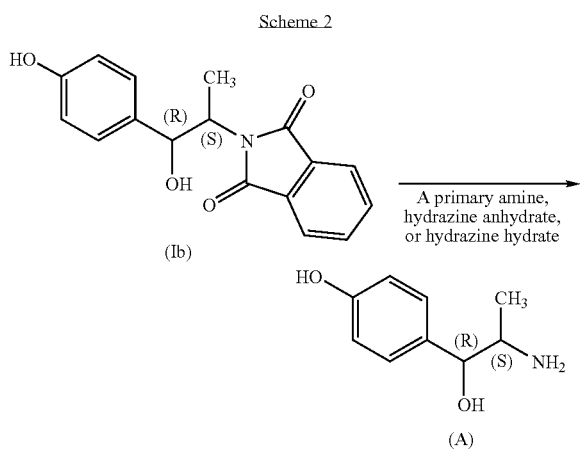

(wherein the carbon atoms marked with (R) and (S) have the same meanings as defined above.)

The compound (A) useful as a production intermediate of medicaments can be obtained by removing the phthaloyl group of the phenol derivative (Ib), for example, to treatment with a primary amine such as methylamine, hydrazine anhydrate or a hydrate thereof in an organic solvent such as ethanol, or water, or a mixed solvent thereof usually at 20° C. to 90° C. usually for 1 to 48 hours. As a primary amine, it is preferable to use 3 to 20 equivalent of methylamine.

For example, the phenol derivative represented by the above formula (A) obtained in Scheme 2 can be derived into a compound useful as a pharmaceutical drug in manners described in the above literatures 1 to 3.

Literature 5: Hoogwater, D. A., and other 4, Synthesis of N-phthaloylamino acids and amino acid esters under mild conditions, 1973, Vol. 92, No. 7, p. 819–825.

EXAMPLES

The present invention is further illustrated in more detail by way of the following Reference Examples, Examples and Test Examples. However, the present invention is not limited thereto.

Example 1

(S)-2-[2-(4-Hydroxyphenyl)-1-methyl-2-oxoethyl]isoindol-1,3-dione

To a mixture of (S)-2-phthalimidopropionic acid (25.0 g) and chlorobenzene (25 mL), thionyl chloride (9.9 mL) was added and the resulting mixture was stirred at 85° C. (external temperature) for 12 hours. (S)-2-phthalimidopropionyl chloride was obtained by removing the solvent in vacuo. To a mixture of alminium chloride (16.7 g) and chlorobenzene (150 mL), anisole (18.6 mL) was added and this mixture was stirred at 60–65° C. (internal temperature). To this mixture, the solution of (S)-2-phthalimidopropionyl chloride, mentioned above, in chlorobenzene (30 mL) was added dropwise over 20 minutes, and the resulting mixture was stirred at 60–65° C. (internal temperature) for 12 hours. After the temperature of the reaction mixture was raised to 70–75° C. (internal temperature), aluminium chloride (45.6 g) was added to this mixture, and then stirred at same temperature for 3 hours. The mixture was cooled to 50° C. (internal temperature) and ethyl acetate (50 mL) was added dropwise. The resulting mixture was added to a mixture of water (250 g), ethanol (25 mL) and ethyl acetate (100 mL) at 30–45° C. (internal temperature), and stirred at same temperature for 30 minutes. Organic layer was separated from the reaction mixture, the organic layer was washed with brine, sodium bicarbonate solution, brine, 1 mol/L hydrochloric acid and brine, and dried over anhydrous sodium sulfate. After removing the solvent in vacuo, the resulting residue was recrystallized from toluene to obtain (S)-2-[2-(4-hydroxyphenyl)-1-methyl-2-oxoethyl]-isoindol-1,3-dione (18.1 g, 53.6% yield, optical purity 99.9% e.e.).

NMR (CDCl$_3$) δ ppm: 1.73 (3H, d J=7.3 Hz), 5.49 (1H, s), 5.62 (1H, d J=7.3 Hz), 6.81 (2H, d J=8.8 Hz), 7.65–7.75 (2H, m), 7.78 (2H, d J=8.8 Hz), 7.8–7.85 (2H, m)

Optical purity of (S)-2-[2-(4-hydroxyphenyl)-1-methyl-2-oxoethyl]isoindol-1,3-dione was measured by the following conditions.
Column: CHIRALCEL OJ 4.6×250 mm
  (Daicel Chemical Industries, LTD.)
Mobile phase: hexane/isopropanol=3/1
Flow rate: 1.0 mL/min.
Column temp.: 30° C.
Detection: UV (230 nm)

Example 2

(1S, 2R)-2-[2-Hydroxy-2-(4-hydroxyphenyl)-1-methylethyl]-isoindol-1,3-dione

To a solution of (S)-2-[2-(4-hydroxyphenyl)-1-methyl-2-oxo-ethyl]isoindol-1,3-dione (17.7 g) in N,N-dimethyl-formamide (60 mL), 10% palladium on carbon (7.1 g: containing 50% w/w water) was added. The mixture was stirred under hydrogen atmosphere (5.0 atm.) at room temperature for 10 hours. After removing insoluble matter by filtration, the filtrate was diluted with water (400 mL) and extracted with ethyl acetate. Organic layer was washed with brine, sodium bicarbonate solution, brine, 1 mol/L hydrochloric acid and brine, and dried over anhydrous sodium sulfate. After removing the solvent, the resulting residue was recrystallized from ethanol/hexane to obtain (1S,2R)-2-[2-hydroxy-2-(4-hydroxyphenyl)-1-methyl-ethyl]isoindol-1,3-dione (16.8 g : 57% yield, optical purity 100% e.e.).

NMR (CD$_3$OD) δ ppm: 1.63 (3H, d J=6.9 Hz), 4.35–4.45 (1H, m), 5.03 (1H, d J=9.5 Hz), 6.54 (2H, d J=8.5 Hz), 7.05 (2H, d J=8.5 Hz), 7.65–7.7 (4H, m)

Optical purity of (1S,2R)-2-[2-hydroxy-2-(4-hydroxyphenyl)-1-methylethyl]isoindol-1,3-dione was measured by the following conditions.
Column: CHIRALPAK AD 4.6×250 mm
  (Daicel Chemical Industries, LTD.)
Mobile phase: hexane/isopropanol=4/1
Flow rate: 0.5 mL/min.
Column temp.: 25° C.
Detection: UV (225 nm)

Example 3

(1R, 2S)-2-Amino-1-(4-hydroxyphenyl)propan-1-ol

To a suspension of (1S,2R)-2-[2-hydroxy-2-(4-hydroxyphenyl)-1-methylethyl]isoindol-1,3-dione (1.0 g) in methanol (1.7 mL), methylamine in methanol (40% w/v; 3.5 mL) was added. The mixture was heated under reflux in argon atmosphere for 12 hours. After removing the solvent in vacua, the resulting residue was dissolved in tetrahydrofuran (3 mL) under heating. This solution was cooled and kept at room temperature. After removing the resulting precipitate by filtration, the mother liquor was concentrated in vacua. The resulting residue was recrystallized from ethyl acetate/methanol to obtain (1R, 2S)-2-amino-1-(4-hydroxyphenyl)propan-1-ol (0.30 g: 54% yield, optical purity 100% e.e.).

NMR (CD₃OD) δ ppm: 1.06 (3H, d J=6.6 Hz), 2.9–3.05 (1H, m), 4.31 (1H, d J=6.0 Hz), 6.76 (2H, d J=8.5 Hz), 7.17 (2H, d J=8.5 Hz)

For determination of optical purity, (1R,2S)-2-amino-1-(4-hydroxyphenyl)propan-1-ol was treated with di-tert-butyl dicarbonate in ethanol and the resulting mixture was concentrated in vacua. The obtained residue was analyzed by the following conditions.

Column: CHIRALPAK AD 4.6×250 mm
(Daicel Chemical Industries, LTD.)
Mobile phase: hexane/isopropanol=4/1
Flow rate: 0.5 mL/min.
Column temp.: 25° C.
Detection: UV (225 nm)

INDUSTRIAL APPLICABILITY

The present invention is to provide a novel intermediate to produce an optically active phenol derivative represented by the above formula (A) useful as a production intermediate of medicaments, and a method to produce the compound (A) using the intermediate. With the production route through the production intermediate of the present invention, an optically active phenol derivative represented by the above formula (A) can be prepared effectively and efficiently. That is preferable in manufacture on an industrial scale and from the view point of environmental aspects.

The invention claimed is:

1. A compound represented by the general formula:

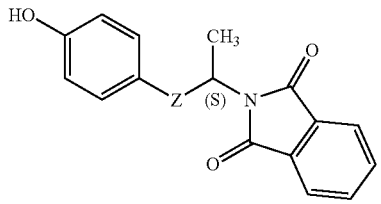

wherein the carbon atom marked with (S) represents a carbon atom in S configuration; Z is the group represented by the formula:

wherein the carbon atom marked with (R) represents a carbon atom in R configuration.

2. A method to produce a compound represented by the formula:

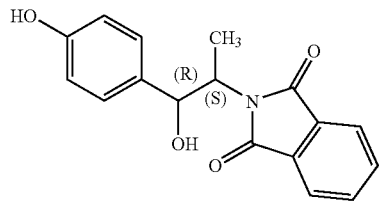

wherein the carbon atom marked with (R) represents a carbon atom in R configuration, and the carbon atom marked (S) represents a carbon atom in S configuration, which comprises catalytic hydrogenating a compound represented by the following formula in the presence of a hydrogenation catalyst:

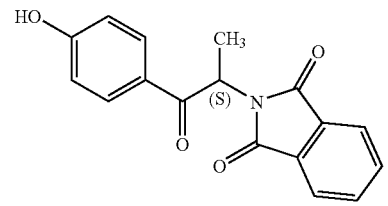

wherein a carbon atom marked with (S) has the same meaning as defined above.

3. A method to produce a compound represented by the formula:

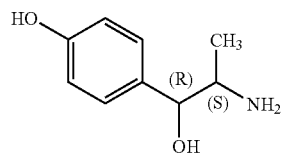

wherein the carbon atom marked with (R) represents a carbon atom in R configuration, and the carbon atom marked (S) represents a carbon atom in S configuration, which comprises removing the phthaloyl group of a compound represented by the formula:

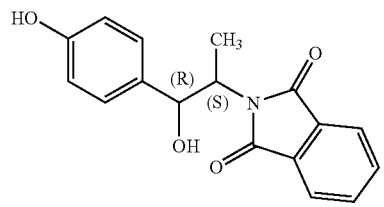

wherein the carbon atoms marked with (R) and (S) have the same meanings as defined above.

4. The method according to claim 2, wherein said hydrogenation catalyst is palladium catalyst or nickel catalyst.

5. The method according to claim 3, wherein the removing of the phthatoyl group is by treatment with a primary amine, hydrazine anhydrate or a hydrate thereof.

* * * * *